United States Patent [19]

Wells

[11] Patent Number: 4,651,008
[45] Date of Patent: Mar. 17, 1987

[54] SAMPLE INLET SYSTEM FOR AN ELECTRON CAPTURE DETECTOR

[75] Inventor: Gregory J. Wells, Suisun, Calif.

[73] Assignee: Varian Associates, Inc., Palo Alto, Calif.

[21] Appl. No.: 529,291

[22] Filed: Sep. 6, 1983

Related U.S. Application Data

[63] Continuation-in-part of Ser. No. 522,081, Aug. 11, 1983, abandoned.

[51] Int. Cl.⁴ ............................................. G01N 27/66
[52] U.S. Cl. ...................................... 250/381; 250/379; 324/465; 324/469; 422/89
[58] Field of Search ............................ 422/89, 90, 54; 436/153, 154; 250/435–438, 379, 381, 384, 389; 324/465, 469

[56] References Cited

U.S. PATENT DOCUMENTS

| | | | |
|---|---|---|---|
| 3,176,135 | 3/1965 | Lovelock | 250/379 |
| 3,361,907 | 1/1968 | Gregory | 250/389 |
| 4,063,156 | 12/1977 | Patterson | 324/465 |
| 4,264,817 | 4/1981 | Neukermans et al. | 324/465 X |

FOREIGN PATENT DOCUMENTS

| | | | |
|---|---|---|---|
| 2547321 | 4/1976 | Fed. Rep. of Germany | 324/469 |
| 0091798 | 8/1978 | Japan | 422/54 |
| 1186525 | 4/1970 | United Kingdom | |
| 0595670 | 3/1978 | U.S.S.R. | 422/54 |
| 0608089 | 5/1978 | U.S.S.R. | 324/469 |
| 0642650 | 1/1979 | U.S.S.R. | 422/89 |
| 0911301 | 3/1983 | U.S.S.R. | 250/381 |

OTHER PUBLICATIONS

Anal. Chem. 1980, 52, 473–482 "Improved Model of the Pulsed Electron Capture Detector", P. L. Gobby, E. P. Grimsrud and S. W. Warden.
J. of Chromatography, 235 (1982) 1–20, "Non-Radioactive Electron-Capture Detector", A. Neukermans, W. Kruger and D. McManigill.

Primary Examiner—Arnold Turk
Attorney, Agent, or Firm—Stanley Z. Cole; David Schnapf

[57] ABSTRACT

An electron capture detector for use with a capillary column is provided with a sample inlet comprising a tubular anode through which sample molecules and a make-up gas are introduced into the detector cell. The tubular anode has side ports for producing a plug-like flow inside the cell. The inner surface of the anode is protected by an insulating tube so that the capillary column can be extended to a point beyond the side ports without the fear of its electrical contact with the anode. This allows the sample molecules to flow nearly entirely in the center section of the cell. The peripheral regions of the cell where a radioactive foil is disposed is swept nearly entirely by the make-up gas entering the cell through the side ports. This has the effects of reducing sample dilution by the make-up gas and sample loss due to contact with the detector walls.

14 Claims, 4 Drawing Figures

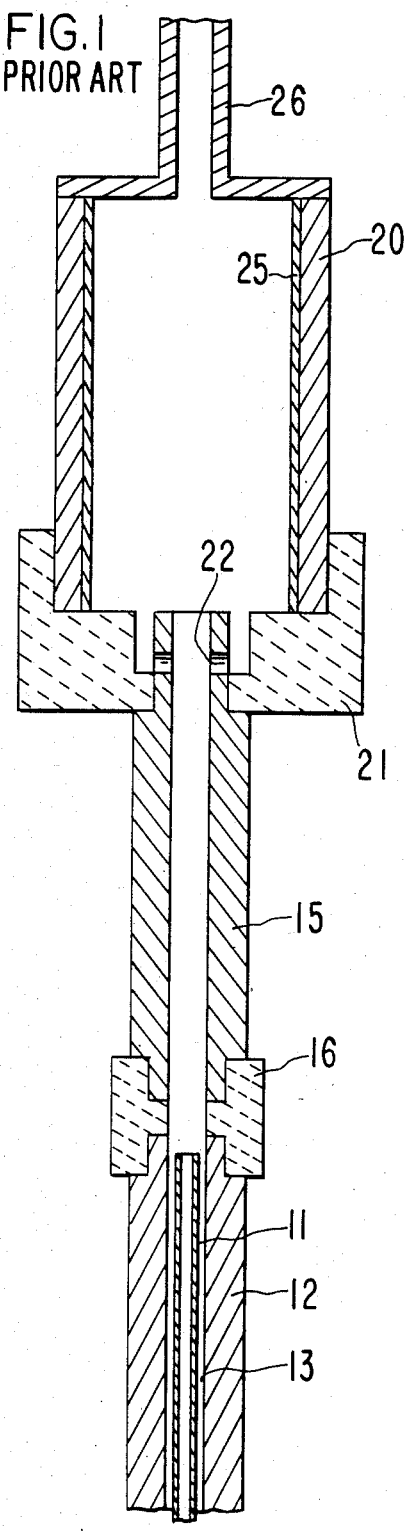
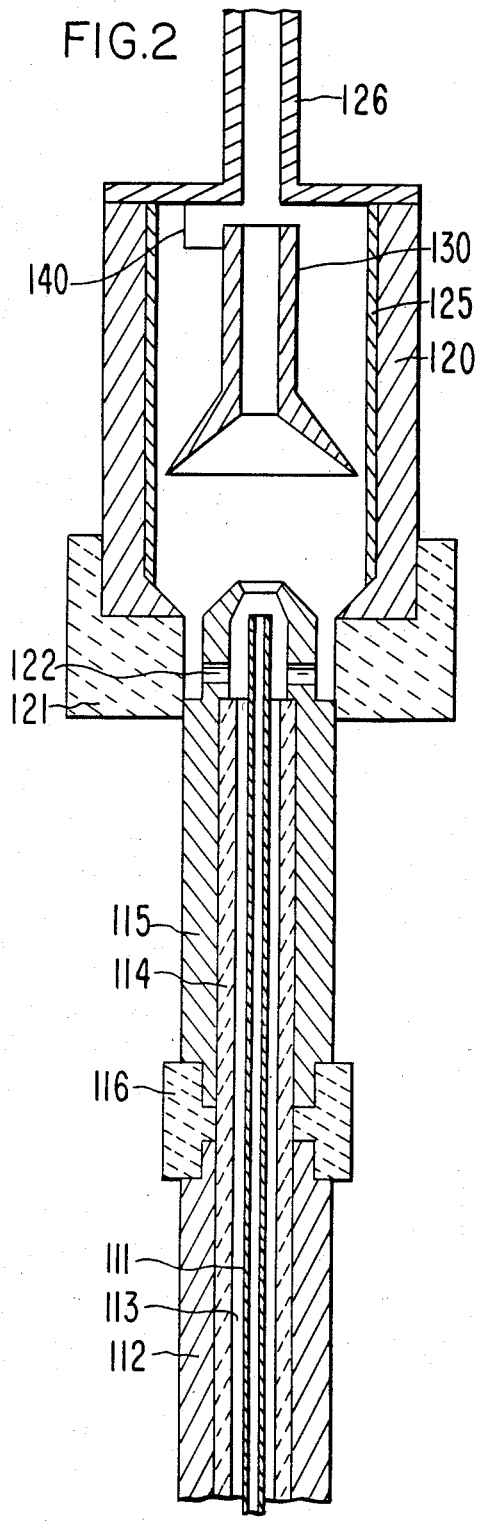

SAMPLE INLET SYSTEM FOR AN ELECTRON CAPTURE DETECTOR

This is a continuation-in-part of application Ser. No. 522,081, filed Aug. 11, 1983, now abandoned.

BACKGROUND OF THE INVENTION

This invention relates generally to a sample inlet system for an electron capture detector for use with high resolution capillary columns in gas chromatography and more in particular to a method of minimizing the sample contact with the metal walls of the detector cell and the dilution of the sample with the make-up gas.

By the electron capture detection technique in gas chromatography, a tritium or Ni$^{63}$ source ionizes the molecules of a carrier of make-up gas as it flows through the detector and the slow electrons thus produced are caused to migrate to the anode, forming a steady or pulsed current. This current becomes reduced if a sample containing electron absorbing molecules is introduced and this loss of current can be amplified by an electrometer for analysis.

The electron capture detector is extremely sensitive to certain molecules such as alkyl halides, but is relatively insensitive to hydrocarbons, alcohols, ketones, etc. This selective sensitivity to halides makes the detection method especially valuable for the trace analysis of many environmentally important organic compounds such as pesticides. There is shown in FIG. 1 the general design of a prior art electron capture detection system such as the commercially available one disclosed by P. L. Patterson in J. Chromatogr., 134 (1977) at page 25). The top portion of a gas chromatography column 11 through which the sample to be analyzed is led nto the detector is housed concentrically inside an inlet tube 12 so as to form a passageway 13 having an annular cross section between the inner wall of the inlet tube 12 and the outer wall of the column 11. This passageway 13 is for a make-up gas, the use of which may become necessary in order to push the column gas (sample with a carrier gas) into the detector, for example, when the column 11 is a capillary column. The make-up gas then becomes mixed with the gas from the column 11. A generally cylindrical metal anode 15 is connected to the upper end of the inlet tube 12, separated therefrom by a ceramic insulator 16. The other end of the anode 15 opens into a cylindrical cell 20 (of length L and diameter D), separated therefrom by another ceramic insulator 21. The top end of the cylindrical anode 15 is provided with side ports 22. Thus, the sample from the column 11 and the make-up gas from the passageway 13 become mixed together as they travel upwards through the cylindrical anode 15, entering the interior of the cell 20 from below, some of this mixed gas passing through the side ports 22. On the inner wall of the cell 20 is a radioactive foil 25 which, for example, may be a Ni$^{63}$ or H$^3$ source. The top of the cell 20 is connected to an exit tube 26.

The prior art electron capture detector of FIG. 1 has several disadvantages. Firstly, because the sample from the column 11 is made to pass through the metal anode 15 before entering the detector cell 20, there results a sample loss by adsorption and this can cause chromatographic peak broadening. Secondly, a sample loss of adsorption occurs also on surfaces within the cell 20 especially when they are activated by hydrogen. Even when hydrogen is not used as the carrier gas, the presence of hot metal or ceramic surfaces with which the sample can come in contact should be expected to have detrimental effects. Thirdly, the make-up gas, when its use is necessary, tends to dilute the sample, decreasing the sensitivity of the detector. Fourthly, the detector cell 20, according to the prior art design as shown, includes regions at the top corners which are not actively swept by the carrier gas. An electron capture detector is generally sensitive to oxygen, and it is therefore necessary to prevent its back diffusion by increasing the length-to-diameter ratio of the exit tube 26. This necessarily tends to enlarge such unswept areas especially when the length-to-diameter ratio (L/D) of the cell 20 is decreased.

For the above and other reasons, electron capture detectors have not been used extensively in conjunction with high resolution capillary columns.

It is therefore a general object of this invention to provide an electron capture detector with a sample inlet system which can reduce the dilution of the sample with the make-up gas which may have to be used.

It is another object of the present invention to provide a small volume electron capture detector cell wherein the mixing volume effects are minimized or eliminated.

It is a further object of the present invention to provide an electron capture detector with a sample inlet system which does not require the sample to pass through a metal anode before entering the active volume of the cell.

SUMMARY OF THE INVENTION

The above and other objects are achieved by providing an insulating tube inside the tubular anode so that the capillary column can extend up to a point beyond the side ports and just below the end of the anode without increasing the probability of electrical contact between the anode and the outer coating of the column. The sample molecules will flow only through the center section of the detector cell and the surface of the radioactive foil will be swept nearly entirely by the make-up gas.

BRIEF DESCRIPTION OF THE DRAWINGS

FIG. 1 is a schematic cross-sectional view of a prior art electron capture detector.

FIG. 2 is a schematic cross-sectional view of an electron capture detector of the present invention.

DETAILED DESCRIPTION OF THE INVENTION

Figure 3:
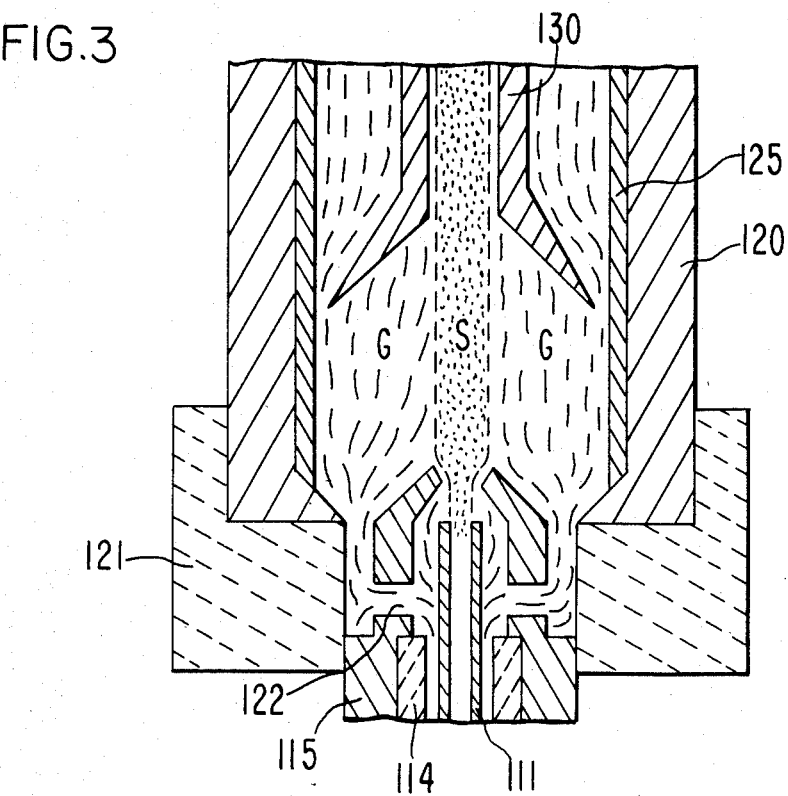
FIG. 3 shows how the sample from the column and the make-up gas are expected to flow through the inlet system and the detector cell of FIG. 2.

An electron capture detection system according to the present invention is shown in FIG. 2 wherein components which are identical or comparable to a component in FIG. 1 are given a three-digit numeral of which the last two are identical to those of the corresponding component in FIG. 1. In this embodiment, an insulating tube 114 of high purity alumina is positioned inside the inlet tube 112 and the anode 115 which are separated by a ceramic insulator 116. This insulating tube 114 extends up to a point just below the side ports 122 which are provided near the top of the anode 115. The gas chromatography column 111 through which the sample is led into the detector extends higher than in FIG. 1 and reaches beyond the side ports 122 so that only the make-up gas introduced through the annular passageway 113 between the outer wall of the column 111 and the inner wall of the insulating tube 114 will enter the detector cell through the side ports 122. These changes in the inlet system from FIG. 1 are intended to cause the make-up gas to sweep the sample only into the central region of the cell, minimizing the sample dilution by preventing the complete mixing with the make-up gas and reducing the contamination by the sample of the radioactive foil 125 which is disposed on the inner wall of the generally cylindrical cell 120. The top of the cell 120 is connected to an exit tube 126.

Placed inside the cell 120 is a metallic structure 130, the purpose of which is to limit the active volume of the detector 120, defined as the region from which electrons are collected for measurement, to below this structure 130, thereby separating the unswept areas from the active volume. For this purpose, this structure 130 is made of a conductive metal and maintained at the same potential as the side walls of the cell 120, or the radioactive foil 125, for example, by an electrical connection 140 to the latter. The structure 130 is generally shaped like a funnel, having a cylindrical section and a cup-shaped section. The cup-shaped section faces the top end of the column 111, while the cylindrical section which servs as a gas conduit, points upward to the exit tube 126. The cup-shaped section is so designed and positioned that its rims are closely adjacent to, but not completely touching, the readioactive foil 125 so that gas can pass through the gap therebetween, although a majority of the gas introduced into the detector cell 120 will be caused to pass through the cylindrical section of the structure 130. Thus, the top corners of the cell 120 which are not actively swept by the carrier gas, and hence previously referred to as the unswept areas, are effectively separated by the structure 130 from the region below which is approximately bounded by the inner surface of the cup-shaped section of the structure 130, a lower portion of the radioactive foil 125 and the top of the inlet system. The inner surface of the cup-shaped section may be tapered appropriately so as to streamline the gas flow through the center. With the insertion of this structure 130, therefore, mixing effects in the top corners of the cell 120 near the exit tube 126 are no longer of any significance because they do not occur within the active region.

FIG. 3 shows schematically and enlarged the top end of the anode 115 as well as how the sample (S) from the column 111 and the make-up gas (G) from the passageway 113 are expected to flow through the detector cell 120. Since the insulating tube 114 serves not only to align the column 111 along the axis of the cell 120, but also to prevent the generally conductive coating on the external wall of the column 111 from contacting the anode 115, the column 111 can be positioned nearly flush with the top of the anode 115. The side ports 122 (as well as 22 of FIG. 1) are for obtaining a nearly plug-like gas flow inside the cell 120, but since the top of the column 111 according to the design of FIG. 2 is positioned thereabove, only the gas from the annular passageway 113 concentrically outside the column 111 (namely, the make-up gas introduced at the bottom of the insulating tube 114) passes through the side ports 122 and forms the peripheral portion of this plug-like flow. A portion of the make-up gas will flow into the cell 120 through the central bore of the anode 115 together with the sample from the column 111. The top end of the anode 115 may be so designed as to be somewhat narrower in order to make a larger fraction of the make-up gas to flow through the side ports 122.

As a result, the gas composition of the plug-like flow is quite different between the cells of FIG. 1 and FIG. 2. While a relatively uniform mixture of the sample and the make-up gas will move into the cell 20 of FIG. 1, both through the side ports 22 and through the opening of the anode 15 at the top because the mixing takes place over the relatively long distance between the top of the column 11 and the side ports 22, the sample in the case of FIGS. 2 and 3 moves only into the central part of the cell 120. As shown in FIG. 3, the peripheral regions in the immediate vicinity of the radioactive foil 125 are swept nearly entirely by the make-up gas. This means both that the sample loss due to adsorption on the foil surface is minimized and that the sample dilution by the make-up gas is reduced.

A major portion of the gas inside the cell 120 is caused to pass through the funnel-shaped structure 130 as described above and illustrated in FIG. 3. Since the active volume of the cell 120 defined as the region where electrons can be extracted by the anode 115 is that part of the cell 120 below the structure 130, the top corners of the cell 120 which are not generally swept actively by the make-up gas are separated from the active volume.

Figure 4:
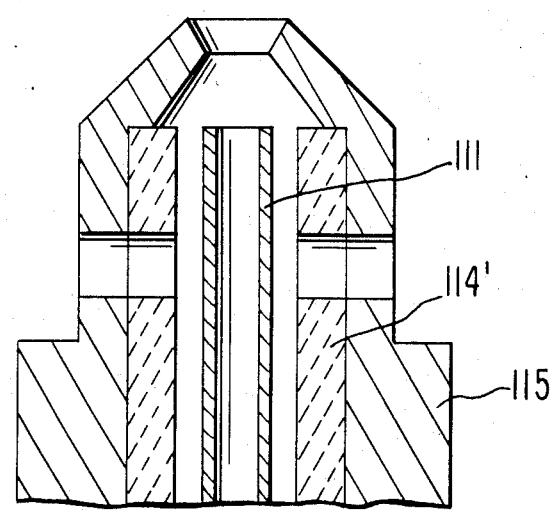
FIG. 4 is a schematic cross-sectional view of another design for the top section of the anode of the detector shown in FIG. 2.

While this invention has been described above in terms of but one embodiment, others are also contemplated as within the scope of this invention. For example, the figures are to be understood merely as being schematically illustrative, rather than as representing the true or preferred dimensional relationships. The geometrical design of the anode 115 including the size and the shape of the side ports 122, may be changed appropriately. As for the insulating tube 114, it may also be made of another high purity, high temperature resistant insulator such as ruby, sapphire or boron nitride. Although it stops short of reaching the side ports 122 according to the design described in FIG. 2, it may be designed to cover points beyond the side ports 122 on the inner surface of the anode 115 as shown in FIG. 4. In such a case, side ports must of course be provided also to the insulating tube 114'. The funnel-like structure 130 may be shaped differently as long as it serves the desired function of separating the unswept regions from the active volume inside the cell 120. For this reason and purpose, the structure 130 may be provided with a metal screen stretched across its rims. The scope of the invention is limited only by the following claims.

What is claimed is:

1. An electron capture detector for use with a gas chromatography column, comprising
    a tubular cell having a generally cylindrical inner wall, an entrance opening and an exit opening,
    a radioactive source disposed on said inner wall,
    gas introduction means associated with the entrance opening for causing a mixture of sample gas and make-up gas to flow into said cell surrounded by a coaxial flow of pure make-up gas such that substantially all said sample gas flows through said cell without contacting said radioactive source; and
    electrode means for detecting current variations as the constituents of said sample gas changes.

2. The detector of claim 1 wherein said gas introduction means comprises a tubular anode stucture having a central aperture and side ports.

3. The detector of claim 1 in which said gas introduction means includes a nozzle means at said entrance opening having a central axial outlet for directing said sample gas centrally axially into said cell, and an annular gas outlet surrounding said central outlet for directing said make-up gas peripherally about said sample gas, so that the region adjacent said radioactive source is swept nearly entirely by a layer of make-up gas.

4. The detector of claim 1 which further includes a streamlined hollow metallic structure adjacent said exit having an enlarged rim facing said gas introduction means, and a reduced outlet section facing said exit end.

5. An electron capture detector and sample inlet therefor comprising:
a column outlet tube having inlet and outlet ends for introducing a sample from a gas chromatography column into an electron capture detector cell having an exit end, the inner surface of said cell supporting a layer of radioactive material;
an insulating tube spaced outside said column outlet tube for introducing a flow of make-up gas, said insulating tube extending toward said cell adjacent to the outlet end of said column outlet tube;
an electrically conductive, hollow anode outside said insulating tube having a central aperture aligned axially with said outlet end of said column outlet tube, said aperture communicating for gas flow with the outlet ends of said column outlet tube, and said insulating tube;
at least one side port for flow of make-up gas from said insulating tube to the outside of said anode;
a coaxial channel outside said anode for conducting said make-up gas from said at least one side port to said cell; and
an insulator sealed between said cell and said anode; whereby a mixture of sample gas and make-up gas flows axially into said cell surrounded by a coaxial flow of pure make-up gas.

6. The system of claim 5 wherein said insulating tube covers nearly entirely the entire inner surface of said anode between said column and said at least one side port.

7. The system of claim 5 wherein said insulating tube is made of a material selected from a group of high purity, high temperature resistant substances consisting of alumina, ruby, sapphire and boron nitride.

8. The system of claim 5 wherein the outlet of said coaxial channel is near said layer of radioactive material such that the flow of make-up gas prevents molecules of said sample gas from contacting said radioactive material.

9. The system of claim 5 wherein said column outlet tube is a portion of said column.

10. The system of claim 5 wherein said insulating tube covers nearly entirely the inner surface of said anode.

11. The system of claim 10 wherein said column outlet tube extends toward said cell beyond said side port.

12. An electron capture detector for use with a chromatographic column, comprising:
a tubular cell having a generally cylindrical inner wall, and a gas exit at one end;
gas nozzle means including an anode at the end of said cell opposite said gas exit, for directing sample-bearing gas centrally axially into said cell, and for separately directing a make-up gas peripherally about said sample-bearing gas, said sample-bearing and make-up gases moving away from said means in a flow which keeps said sample-bearing gas axially confined;
streamlined apertured metallic means in electrical contact with said inner wall acjacent said exit for limiting the active internal cell volume for electron capture detection to a region adjacent said nozzle, while isolating said region from other regions adjacent said exit wherein said flow may be disturbed by mixing effects; and
a radioactive source disposed on said inner wall and extending into at least a portion of said active internal cell volume.

13. An electron capture detector as in claim 12, in which said nozzle means defines an annular channel opening into said cell, and a centrally axially directed aperture, said annular channel surrounding said central aperture, said sample-bearing gas being emitted from said axially directed aperture, said make-up gas being emitted from said annular channel to form the peripheral portion of said plug-like flow.

14. An electron capture detector as in claim 12, in which said metallic means is a hollow structure with its largest diameter facing said nozzle, said diameter being a substantial fraction of the diameter of said cell inner wall, and with a reduced diameter facing said gas exit.

* * * * *